United States Patent [19]

Smithers

[11] Patent Number: 4,925,869

[45] Date of Patent: May 15, 1990

[54] THERAPEUTIC AGENTS

[75] Inventor: Michael J. Smithers, Macclesfield, United Kingdom

[73] Assignee: Imperial Chemical Industries PLC, London, United Kingdom

[21] Appl. No.: 118,227

[22] Filed: Nov. 3, 1987

[30] Foreign Application Priority Data

Nov. 4, 1986 [GB] United Kingdom ............... 8626296

[51] Int. Cl.$^5$ ........................................... A61K 31/075
[52] U.S. Cl. ..................................... 514/452; 549/369
[58] Field of Search ...................... 514/452; 549/369; 568/611, 593, 583, 649

[56] References Cited

FOREIGN PATENT DOCUMENTS 2111050  6/1983  United Kingdom .

OTHER PUBLICATIONS

J. Med. Chem., 1985, 28, 1427–1432; Cross et al.
J. Med. Chem., 1986, 29, 1461–1468; Johnson et al.
J. Med. Chem., 1986, 29, 342–346; Cross et al.
Br. J. Pharmac., 1985, 86, 497–504; Ambler et al.
J. Med. Chem., 1985, 28, 165–170; Ford et al.
J. Med. Chem., 1981, 24, 1139–1148; Iizuka et al.
Journal of Medicinal Chemistry, 1981, vol. 24, No. 10; 1149–1155; Tanouchi et al.
J. Med. Chem., 1985, 28, 287–294; Kato et al.
J. Med. Chem., 1986, 29, 523–530; Wright et al.
Antihypertensive Drugs (4410–4415).
Arzneim.-Forsch/Drug Res. 36(I), No. 1 (1986), Sincholle et al.
J. Med. Chem., 1987, 30, 1812–1818; Manley et al.

Primary Examiner—Amelia Burgess Yarbrough
Attorney, Agent, or Firm—Cushman, Darby & Cushman

[57] ABSTRACT

The invention concerns novel therapeutic agents containing a (Z)-(2-alkoxyalkyl- or 2-aryloxyalkyl-4-phenyl-1,3-dioxan-5-yl)alkenoic acid, or a related tetrazole derivative, which antagonizes one or more of the actions of thromboxane $A_2$, together with a compound which inhibits the synthesis of thromboxane $A_2$. The compositions are useful as medicines in treating a variety of diseases or medical conditions in which thromboxane $A_2$ and/or other prostanoid contractile substances are involved.

14 Claims, No Drawings

THERAPEUTIC AGENTS

This invention concerns novel therapeutic agents and, more particularly novel pharmaceutical compositions comprising a novel (2-alkoxyalkyl- or 2-aryloxyalkyl-4-phenyl-1,3-dioxan-5-yl)alkenoic acid or a related tetrazole derivative, which antagonises one or more of the actions of thromboxane $A_2$ (hereafter referred to as "$TXA_2$") together with a compound which inhibits the synthesis of $TXA_2$ (hereafter referred to as a $TXA_2$ synthetase inhibitor). Such compositions are useful as medicines.

It is known that the arachidonic acid metabolite thromboxane $A_2$ is a powerful vasoconstrictor and a potent aggregator of blood platelets. $TXA_2$ is also a potent constrictor of bronchial and tracheal smooth muscle. $TXA_2$ is believed to be involved in a variety of diseases and medical conditions, for example ischaemic heart disease (such as myocardial infarction), angina, cerebrovascular disease (such as transient cerebral ischaemia, migraine and stroke), peripheral vascular disease (such as atherosclerosis, microangiopathy), hypertension and in blood clotting defects due to lipid imbalance.

It is believed that $TXA_2$ exerts its physiological action through the thromboxane receptor, at which receptor various other prostanoid contractile substances derived from arachidonic acid, such as prostaglandins $H_2$, $F_2$ alpha and prostaglandin $D_2$, can exert contractile effects. There are two principal ways in which the effects of $TXA_2$ (and also of prostaglandins $H_2$, $F_2$ alpha and/or $D_2$) can be ameliorated. The first is by administering a pharmacological agent which preferentially occupies the thromboxane receptor, but yet does not produce the contractile effects which follow the binding of $TXA_2$ (or of prostaglandins $H_2$, $F_2$ alpha and/or $D_2$). Such an agent is said to possess $TXA_2$ antagonist properties. The second way is to administer a pharmacological agent which inhibits one or more of the enzymes involved in the production of $TXA_2$ and in particular, which inhibits the enzyme known as thromboxane synthetase ($TXA_2$ synthetase). Such an agent is said to be a $TXA_2$ synthetase inhibitor.

Accordingly, compositions which contain active ingredients which antagonise the actions of $TXA_2$ and which inhibit the production of $TXA_2$ may be expected to have therapeutic value in the prevention or treatment of any one or more of the above mentioned diseases or any other medical conditions in which $TXA_2$ and/or prostaglandins $H_2$, $F_2$ alpha and/or $D_2$ are involved, including asthamtic and inflammatory diseases.

It is known from European patent application, publication No. 94239 that certain 4-phenyl-1,3-dioxan-5-ylalkenoic acids possess $TXA_2$ antagonist properties.

According to the invention there is provided a pharmaceutical composition comprising as active ingredients: (i), a novel 1,3-dioxane ether of the formula I set out hereinafter wherein $R^1$ is (1-6C)alkyl, (3-8C)cycloalkyl, (3-8C)cycloalkyl-(1-4C)alkyl, phenyl or phenyl-(1-4C)alkyl, the latter two of which may optionally bear one or two substituents selected from halogeno, (1-4C)alkyl, (1-4C)alkoxy, hydroxy, trifluoromethyl, nitro and cyano; $R^2$ and $R^3$ are independently hydrogen or (1-4C)alkyl, or together form (3-6C)polymethylene optionally bearing one or two (1-4C)alkyl substituents; n is 1 or 2; m is 2, 3 or 4; p is zero, 1 or 2; Z is carboxy or 1(H)-tetrazol-5-yl and the groups at positions 2, 4 and 5 of the dioxane ring have cis relative stereochemistry; or a pharmaceutically acceptable salt thereof: and (ii), an inhibitor of the synthesis of thromboxane $A_2$ (hereinafter referred to as a $TXA_2$ synthetase inhibitor); together with a pharmaceutically acceptable diluent or carrier.

In the chemical formulae shown hereinafter, although a particular relative configuration is shown, it is to be understood that this is not necessarily the absolute configuration.

The compounds of formula I contain at least three asymmetric carbon atoms and may exist and be isolated in racemic and optically active forms. It is to be understood that the active ingredient (i) can be any racemic, or optically active form, or mixture thereof, of a compound of formula I which is capable of antagonising one or more of the actions of $TXA_2$, it being well known in the art how to prepare individual optical isomers (for example by synthesis from optically active starting materials or resolution of a racemic form), and how to determine the $TXA_2$ antagonist properties using the standard tests described hereafter.

A preferred value for n is 1 and for m is 2 or 3.

A particular value for $R^1$ when it is (1-6C)alkyl is, for example, methyl, ethyl, propyl, or butyl: when it is (3-8C)cycloalkyl is, for example, cyclopropyl, cyclobutyl, cyclopentyl or cyclohexyl: when it is (3-8C)cycloalkyl-(1-4C) alkyl is, for example, cyclopropylmethyl, cyclopentylmethyl or cyclohexylmethyl; and when it is phenyl-(1-4C)alkyl is, for example, benzyl or 2-phenylethyl.

A particular value for $R^2$ or $R^3$ when either is (1-4C)alkyl is, for example, methyl or ethyl.

In general it is preferred that when $R^2$ and $R^3$ are both alkyl, they total together up to 6 carbon atoms.

A particular value for an optional (1-4C)alkyl substituent when $R^2$ and $R^3$ form (3-6C)polymethylene (for example trimethylene or tetramethylene) is, for example, methyl.

Particular values for optional substituents which may be present as part of $R^1$, when it is phenyl or phenyl-(1-4C) alkyl are for example:

for halogeno: fluoro, chloro or bromo;
for (1-4C)alkyl: methyl or ethyl; and
for (1-4C)alkoxy: methoxy or ethoxy.

A preferred group of compounds which is of particular interest as active ingredient (i) comprises those [2,4,5-cis]dioxane derivatives of formula II wherein $R^5$ is (1-4C)alkyl (such as methyl, ethyl or propyl), (3-8C)cycloalkyl (such as cyclopetyl or cyclohexyl) or phenyl, the latter optionally bearing a substituent selected from halogeno (such as chloro or bromo), (1-4C)alkyl (such as methyl), (1-4C)alkoxy (such as methoxy), nitro and cyano; q is 2 or 3; $R^6$ and $R^7$ are independently hydrogen or methyl; and Z is carboxy or 1(H)tetrozol-5-yl; and the pharmaceutically acceptable salts thereof.

A preferred value for Z is, for example, carboxy. A preferred value for $R^5$ is, for example propyl or phenyl. A particularly preferred value for q is 2. Specific compounds of formula I are described in the accompanying Examples. However, of these, three compounds of particular interest as active ingredient (i) are the carboxylic acids described in Examples 6, 7 or 9, or a pharmaceutically acceptable salt thereof.

Particular pharmaceutically acceptable salts of compounds of formula I are, for example, alkali metal and alkaline earth metal salts, such as lithium, sodium, potassium, magnesium and calcium salts, raluminium and ammonium salts, and salts with organic amines and quaternary bases forming physiologically acceptable cations, such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethyl-ammonium hydroxide.

Suitable $TXA_2$ synthetase inhibitors for inclusion as active ingredient (ii) in the compositions according to the invention include, for example, the known compounds:

(1) dazoxiben (R. P. Dickinson, *J.Med.Chem.* 1985, 28, 1427-1432);
(2) furegrelate [U63557] (R. A. Johnson, *J.Med.Chem.*, 1986, 29, 1461-1468);
(3) UK 38485 (R. P. Dickinson, *J.Med.Chem.*, 1986, 29, 342 346):
(4) CGS 12970 (J. Ambler, *Brit.J.Pharmacol.*, 1985, 86, 497-504):
(5) CGS 13080 (L. Browne, *J.Med.Chem.*, 1985, 28, 164-170);
(6) CGS 14854 (European Patent Appln., Publication No. 80154: Example 7);
(7) OKY 046 (K. Iizuka, *J.Med.Chem.*, 1981, 24, 1139-1148);
(8) OKY 1580 (M. Hayashi, *J.Med.Chem.*, 1981, 24, 1149-1155);
(9) OKY 1581 (M. Hayashi, *J.Med.Chem.* 1981, 24. 1149-1155)
(10) CV 4151 (S. Terao, *J.Med.Chem*, 1985, 28, 287-294);
(11) N [-(1H imidazol-1-yl)octyl]4-chlorobenzamide *J.Med.Chem.*, 1986, 29, 523-530);
(12) CBS 645 (D. Sincholle, *Arzneimittel Forsch.*, 1986, 36, 117-119);
(13) SC 41156 (F. G. Spokas, *Fed.Proc.*, 1986, 45, 913);and
(14) Y20811 (Y. Muramoto, *Japanese J. Pharmacology*, 1986, 40,178P;

or a pharmaceutically acceptable salt thereof [Note: the structures of these $TXA_2$ synthetase inhibitors are given on the attached sheets A and B hereinafter.]

However, any $TXA_2$ synthetase inhibitor which is chemically compatible with the active ingredient (i) may be used in the compositions of the invention.

Particularly suitable $TXA_2$ synthetase inhibitors include, for example, dazoxiben (1), CV4151(10), and the pharmaceutically acceptable salts thereof.

The compounds of formula I may be manufactured by conventional procedures of organic chemistry well known in the art for the manufacture of structurally analogous compounds. Such procedures are illustrated by the following processes in which $R^1$, $R^2$, $R^3$, $R^4$, Z, n, m and p have any of the meanings herein above:

(a) An aldehyde of the formula III is reacted with a Wittig reagent of the formula IVa or IVb wherein R' is (1-6C) alkyl or aryl (especially phenyl) and M+ is a cation, for example an alkali metal cation, such as the lithium, sodium or potassium cation.

The process in general produces predominantly the required compounds of formula I in which the substituents adjacent to the double bond have cis-relative stereochemistry i.e. the "Z" isomer. Any analogous compounds having transrelative stereochemistry about the vinylene group may be removed by a conventional separation procedure, for example by chromatography or crystallisation.

The process is conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, $-80°$ C. to $40°$ C., but is conveniently performed at or near room temperature, for example in the range $0°$ to $35°$ C.

(b) For a compound of formula I wherein Z is 1(H)tetrazol-5-1yl, a nitrile of the formula V is reacted with an azide.

A particularly suitable azide is, for example, an alkali metal azide such as sodium or potassium azide, preferably together with an ammonium halide, for example ammonium chloride, ammonium bromide or triethylammonium chloride. The process is preferably carried out in a suitable polar solvent, for example N,N-dimethylformamide or N-methylpyrrolidone and, conveniently, at a temperature in the range, for example, $50°$ to $160°$ C.

(c) A phenol derivative of the formula VI, wherein R" is (1-6C)alkyl (such as methyl or ethyl), acyl (such as acetyl, benzoyl, methanesulphonyl or p-toluene-sulphonyl), allyl, tetrahydropyran-2-yl or trimethylsilyl, is deprotected.

The precise deprotection conditions used depend on the nature of the protecting group R". Thus, for example, when it is methyl or ethyl the deprotection may be carried out by heating with sodium thioethoxide in a suitable solvent (such as N,N-dimethylformamide or 1,3-dimethyl-3,4,5,6-tetrahydro-2(1H) pyrimidinone)at a temperature in the range, for example, $60°-160°$ C. Alternatively, an ethyl or methyl protecting group may be removed by reaction with lithium diphenylphosphide in a suitable solvent (such as tetrahydrofuran or t-butyl methyl ether) at a temperature in the range, for example, $0°-60°$ C. When the protecting group is acyl it may be removed, for example, by hydrolysis in the presence of a base (such as sodium or potassium hydroxide) in a suitable aqueous solvent [such as an aqueous (1-4C)alkanol] at a temperature in the range, for example, $0°-60°$ C. When the protecting group is allyl or tetrahydropyran-2-yl, it may be removed, for example, by treatment with strong acid (such as trifluoroacetic acid), and when it is trimethylsilyl, it may be removed, for example, by reaction with aqueous tetrabutylammonium fluoride or sodium fluoride, using a conventional procedure.

(d) An erythro-diol derivative of the formula VII, wherein one of $Q^1$ and $Q^2$ is hydrogen and the other is hydrogen or a group of the formula -CRaRb.OH (wherein Ra and Rb are the same or different (1-4C alkyl), is reacted with an aldehyde of the formula VIII wherein $R^1$, $R^2$, $R^3$ and p have the meanings defined above, or with an acetal, hemiacetal or hydrate thereof.

The aldehyde of formula VIII [or its hydrate, or its acetal or hemiacetal with a (1-4C)alkanol (such as methanol or ethanol)] is generally used in excess.

The reaction is generally performed in the presence of an acid catalyst, such as hydrogen chloride, hydrogen bromide, sulphuric acid, phosphoric acid, methanesulphonic acid, p-toluenesulphonic acid or an acidic resin, conveniently in the presence of a suitable solvent or diluent, such as toluene, xylene or an ether, for example tetrahydrofuran, dibutyl ether, methyl t-butyl ether or 1,2-dimethoxy-ethane, and at temperature in the range, for example 0° to 80° C.

Those starting materials of formula VII wherein $Q^1$ and $Q^2$ are both hydrogen may be obtained, for example, by mild acid catalysed hydrolysis or alcoholysis of the dioxane ring of a compound of formula IX wherein Ra and Rb are both alkyl, such as methyl or ethyl. The hydrolysis or alcoholysis will normally be carried out at a temperature in the range 10° to 80° C. using an aqueous mineral acid such as hydrochloric acid, in an alkanol (such as ethanol or 2-propanol) or an ether (such as tetrahydrofuran) as solvent.

The starting materials of formula VII wherein one of $Q^1$ and $Q^2$ is hydrogen and the other is a group of the formula -CRaRb.OH are intermediates in the above-mentioned formation of the starting materials of formula VII wherein $Q^1$ and $Q^2$ are both hydrogen. However, the said intermediates are not normally isolated or characterised. Accordingly, a convenient modification of process (d) comprises reacting a compound of formula IX wherein one of Ra and Rb is hydrogen, methyl or ethyl (preferably methyl or ethyl) and the other is methyl or ethyl with an excess of a compound of the formula VIII, or an acetal, hemiacetal or hydrate thereof, in the presence of an acidcatalyst(such as one of those given above), conveniently at a temperature in the range, for example, 10° to 80° C. and optionally in the presence of a suitable solvent or diluent (such as one of those given above).

The starting materials for use in the above processes may be made by general procedures of organic chemistry, known for the preparation of structurally related compounds, for example as described in European patent application, publication No. 94239.

The nitriles of formula V may be obtained, for example, by substituting the appropriate ylid of the formula $R'_3P=CH.(CH_2)_m.CN$ for the ylid of formula IV in the Wittig reaction described in process (a) above. The protected phenol derivatives of formula VI may be made, for example, by using an analogous procedure to process (a) above, using an aldehyde analogous to formula III but wherein the phenol group has been protected with the group R''. The starting materials of formula IX may be obtained using analogous procedures to those described in European patent application, publication number 94239.

The necessary Wittig reagents of formula IVa and IVb may be obtained by conventional procedures, for example by treating the corresponding phosphonium halides with a strong base, such as sodium hydride, lithium diisopropylamide, potassium t-butoxide or butyllithium. They are generally formed in situ just prior to carrying out the condensation process (a) above.

It will be understood that the compounds of formula I wherein Z is carboxy may also be obtained by other conventional procedures well known in the art for the production of carboxylic acids, for example by base-catalysed hydrolysis of the corresponding esters, for example, the lower alkyl esters, using, for example, lithium or sodium hydroxide as the base. Such procedures are included within the invention.

When a salt of a compound of formula I is required, it is obtained by reaction with the appropriate base affording a physiologically acceptable cation, or by any other conventional procedure.

Further, when an optically active form of a compound of formula I is required, one of the aforesaid processes is carried out using an optically active starting material. Alternatively, the racemic form of a compound of formula I may be reacted with an optically active form of a suitable organic base, for example ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

As stated earlier, the compounds of formula I are antagonists of one or more of the actions of $TXA_2$, for example certain of its actions on blood platelets, the vasculature and/or the lung. The antagonism may be demonstrated in one or other of the following standard tests:

(a) The rabbit aortal strip model devised by Piper and Vane (Nature, 1969, 223, 29–35) or the rat aortal strip model developed by Kennedy et alia (Prostaglandins, 1982, 24, 667–689), using as agonist the $TXA_2$ mimetic agent known as U46619 (described by R. L. Jones et alia. in "Chemistry, Biochemistry and Pharmacological Activity of Prostanoids" edited by S. M. Roberts and F. Scheinmann, at page 211, Pergamon Press, 1979);

(b) a blood platelet aggregation test based on that described by Born (Nature, 1962, 194, 927–929) and involving:

(i) aggregating human, citrated platelet rich plasma by addition of the $TXA_2$ mimetic agent U46619 so that a dose-response curve is generated:

(ii) generating a dose-response curve for U46619 stimulated platelet aggregation in the presence of increasing amounts of test compound (generally in the range, $10^{-5}M$ to $10^{-10}M$); and (iii) calculating a $K_B$ value indicating potency of $TXA_2$ antagonism for the test compound, averaged over several concentrations, from the calculated 50% response value for U46619 aggregation in the presence and absence of test compound: and (c) a bronchoconstriction test involving measuring the inhibition by test compound of the bronchoconstriction induced in the Konzett-Rossler, anaesthetised guinea-pig model (as modified by Collier and James, Brit. J. Pharmacol., 1967, 30, 283–307) by intravenous administration of the $TXA_2$ mimetic agent, U46619 and involving:

(i) obtaining a cumulative dose response curve to U46619 induced bronchoconstriction by intravenous administration of constant volumes of increasing concentrations of U46619 (0.2–4 µg/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose ratio for the test compound (that is the ratio of concentration of U46619 required to cause 50% bronchoconstriction in the presence and absence of test compound) indicating the potency of $TXA_2$ antagonism.

(d) The antagonism of the effects of $TXA_2$ on the vasculature may be demonstrated, for example in rats in the following manner:

Male rats (Alderley Park strain) are anaesthetised with sodium pentobarbital and blood pressure is monitored at the carotid artery. The TXA$_2$ mimetic agent U46619 is administered intravenously via the jugular vein at 5 μg/kg to induce a 20–30 mm Hg (2640–3970 pascal) increase in systolic blood pressure. The process is repeated twice to establish reproducibility of response.

A test compound is then administered either intravenously via the jugular vein or orally via a cannula directly into the stomach and the animal challenged with an U46619 five minutes after dosing with test compound and then successively every ten minutes until the hypertensive effect of U46619 is no longer blocked.

Further, the antagonism of the effects of TXA$_2$ in vivo may be demonstrated, for example, by assessing the effects of a test compound on the aggregation of blood platelets obtained after administration of test compound to a test animal such as a rabbit, rat, guinea pig or dog, using standard procedures similar to that described in (a) above. However, when the aggregation of dog platelets is being studied it is necessary to use a pre-determined, threshold concentration of the platelet aggregrant adenosine diphosphate (about $0.4–1.2 \times 10^{-6}$M) together with the TXA$_2$ mimetic agent, U46619.

By way of illustration, the compound described in Example 6 hereafter possesses a pA$_2$ of 9.71 on rat aortal strip using procedure (a) and exhibits a K$_B$ of $1.75 \times 10^{-8}$M in procedure (b) above.

In general, compounds of formula I show significant TXA$_2$ antagonist properties in one or more of the above mentioned tests i.e. test (a) pA$_2 < 6.0$; test (b) K$_B > 5 \times 10^{-6}$; test (c) dose ratio $<5$ at 200 μg/kg p.o. In addition compounds of formula I may show significant activity in the rat blood pressure test and/or tin one or more of the ex vivo blood platelet tests referred to above. No significant adverse effects have been observed at the active doses in vivo.

The beneficial effects of combining one of the novel TXA$_2$ antagonists of formula I defined hereinabove with a TXA$_2$ synthetase inhibitor may be illustrated in vitro, for example by evaluating their effects in inhibiting arachidonic acid induced aggregation of human platelets, using standard procedures well known in the art.

Thus, for example, the TXA$_2$ antagonist described in Ex.6 hereinafter and the TXA$_2$ synthetase inhibitor known as dazoxiben show no significant inhibition of arachidonic acid induced aggregation of human platelets when tested alone at a concentration of $10^{-9}$M (Ex.6) and $10^{-4}$M (dazoxiben), respectively. However, when these concentrations of antagonist and inhibitor are used together, essentially complete inhibition of aggregation is produced.

These results show that these compounds together exert a synergistic effect, which is illustrative of the expected beneficial effect to be obtained in vivo from co-administration of a novel TXA$_2$ antagonist of formula I with a TXA$_2$ synthetase inhibitor. Such a beneficial effect in vivo may also be demonstrated in laboratory animals, for example by reducing or preventing the adverse effects of platelet aggregation in rabbits following intravenous injection of arachidonic acid.

The invention also embraces a method of medical treatment of one or more diseases in which TXA$_2$ and/or prostaglandins H$_2$, F$_2$ alpha and/or D$_2$ are involved, which comprises administering to a warm-blooded animal a novel TXA$_2$ antagonist of the formula I, or a pharmaceutically acceptable salt thereof, as defined hereinbefore, and a TXA$_2$ synthetase inhibitor, for example as stated hereinbefore. Although it is envisaged that the antagonist and inhibitor will generally be administered at the same time and combined in a single composition, they may also be administered in separate compositions, by different routes and at different times, in order to maximise the therapeutic effect.

As stated previously, the compositions of the invention may be used in the therapy or prevention of diseases or adverse conditions in warm blooded animals in which it is desirable to antagonise one or more of the actions of TXA$_2$ and to inhibit its synthesis. In general, they will be administered for this purpose by an oral, rectal, intravenous, subcutaneous, intramuscular or inhalation route, so that a dose of the active ingredient (i) in the range, for example 0.01–15 mg/kg body weight (and, more particularly, 0.1–5 mg/kg body weight), is received four times per day, varying with the route of administration, the severity of the condition and the size and age of the patient under treatment.

The quantity of the TXA$_2$ synthetase inhibitor, present as active ingredient (ii) in the composition will necessarily vary with its potency as an inhibitor, but will typically be in such an amount that a dose of the active ingredient (ii) in the range, for example 0.05–25 mg/kg body weight, (and, more particularly, 0.5–10 mg/kg body weight), is received up to four times per day, varying with the route of administration, the severity of the condition and the size and age of the patient under treatment.

A unit dose of a composition of the invention will generally contain an amount of each of the active ingredients (i) and (ii) sufficient to provide a single dose of (i) or (ii), as specified above. However because of the expected synergistic effects of co-administering (i) and (ii) to warm-blooded animals (including man), reduced amounts of the individual active ingredients may generally be used. A unit dose will, however, generally contain, for example, 0.5–1200 mg of active ingredient (i) together with 2.5–2000 mg of active ingredient (ii).

The compositions may be in a variety of dosage forms. For example, they may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder together with pharmaceutically acceptable inert solid diluents such as lactose, for administration by insufflation.

The compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The compositions of the invention may also be used because of their combined TXA$_2$ antagonist and TXA$_2$ synthetase inhibitory properties in helping to maintain the viability of blood and blood vessels in warm-blooded animals (or parts thereof) under-going artificial extracorporeal circulation, for example during limb or organ transplant.

The preparation of the compounds of formula I is illustrated by the following Examples 1–9 and the compositions of the invention by the following, non-limiting Example 10. In these Examples, unless otherwise stated:

(i) evaporations were carried out by rotary evaporation in vacuo:

(ii) operations were carried out at room temperature, that is in the range 18°–26° C.;

(iii) flash column chromatography and medium pressure liquid chromatography (MPLC) were performed on Merck Kieselgel 60 (Art, 9385), monitoring the process by UV absorption or thin layer chromatography on Merck 0.25 mm Kieselgel 60F 254 plates (Art. 5715); these materials were obtained from E. Merck, Darmstadt, W. Germany;

(iv) yields are given for illustration only and are not necessarily the maximum attainable;

(v) NMR spectra were normally determined at 200 MHz in $CDCl_3$ using tetramethylsilane (TMS) as an internal standard, and expressed as chemical shifts (delta values) in parts per million relative to TMS using the following abbreviations for designation of major peaks: s, singlet: m, multiplet; t, triplet: b, broad: d, doublet: when a single chemical shift value is given for a multiplet (m) this corresponds to the centre point of the signals making up the multiplet; and (vi) end products were isolated as racemates, and characterised by NMR, microanalysis, mass spectroscopy and or other standard procedures.

EXAMPLE 1

A solution of 5(Z)-7-([2,4,5-cis]-2-methoxymethyl-4-o-methoxyphenyl-1,3-dioxan-5-yl)heptenoic acid (1.80 g) in dry 1,3-dimethyl-3,4,5,6-tetrahydro-2(1H)-pyrimidinone (DMPU) (4 ml) was added to a stirred solution of sodium thioethoxide (2.47 g) in dry DMPU (50 ml) at 85° C. under argon. The mixture was stirred for 2 hours, cooled to ambient temperature and poured into ice-water (150 ml). The aqueous mixture was washed with dichloromethane (2×75 ml), acidified to pH4 with 2M hydrochloric acid and extracted with ether (3×100 ml). These extracts were washed successively with water (3×50 ml) and saturated brine (50 ml), then dried ($MgSO_4$) and evaporated. Flash chromatography of the residue, eluting with toluene/ethyl acetate/acetic acid (75:25:02 vv) gave 5(Z)-7-([2,4,5-cis]-4-o-hydroxyphenyl-2-methoxymethyl-1,3-dioxan-5-yl)heptenoic acid, as a pale yellow oil (1.01 g); NHR: 1.63 (3H,m), 1.87 (1H,m), 2.00 (2H,q J=7 Hz), 2.28 (2H, t J=7 Hz), 2.62 (1H,m), 3.45 (3H,s), 3.60 (2H,m), 3.93 (1H,dm J=12, Hz), 4.14 (1H,dd J=12, 1 Hz), 4.94 (1H,t J=5 Hz), 5.25 (1H,d J=2 Hz), 5.34 (2H,m), 6.90 (3H,m), 7.17 (1H,m); m/e 350 (M+).

The necessary starting material was obtained as follows:

(i) A solution containing 5(Z)-7-(2,2-dimethyl-4 -o-methoxyphenyl-1,3-dioxan-cis-5-yl)heptenoic acid (10.0 g), water (33 ml) and 2H hydrochloric acid (0.5 ml) in tetrahydrofuran (THF) (267 ml) was heated with stirring at 60°–70° C. for 2 hours. The solvent was then evaporated. The residue obtained was diluted with ether (350 ml). The mixture was washed with water (4×75 ml), then with saturated brine (2×75 ml), dried ($MgSO_4$) and evaporated. The oil obtained was purified by flash chromatography, eluting with toluene/ethyl acetate/acetic acid (60:40:2 vv,v), to give 5(Z) ervthro-9-hydroxy-8-hydroxymethyl-9-o methoxyphenyl-5 nonenoic acid as a colourless oil which slowly crystallised to give solid (A) (8.40 g), m.p. 79°–80° C.: NMR (400 MHz): 1.66 (2H,m), 1.90 (1H.m), 2.08 (3H,m), 2.32 (3H,m), 3.69 (2H,m), 3.82 (3H,s), 5.22 (1H,d J=4 Hz), 5.37 (2H,m), 6.88 (1H,d J=8 Hz), 6.98 (1H,t J=7 Hz), 7.25 (1H,m), 7.43 (1H,dd) J=7,2 Hz). (ii) A solution containing A (7.70 g) and ethyl acetate (10 ml) in ether (25 ml) was treated at 4° C. with an ice-cold ethereal solution of diazomethane until a yellow colour persisted. The solution was then treated with acetic acid (0.2 ml) and the solvent removed in vacuo. The residual oil was purified by flash chromatography, eluting with 45% v/v ethyl acetate/hexane, to give methyl 5(Z) ervthro-9-hydroxy-8-hydroxymethyl-9-o-methoxyphenyl-5-nonenoate as a colourless oil (B) (7.83 g): NMR (400 MHz): 1.74 (2H,m), 1.89 (1H,m), 2.05 (3H,m), 2.30 (3H,m). 2.47 (1H,br s), 3.13 (1H,d J=4 Hz). 3.66 (3H,s), 3.68 (2H,m), 3.84 (3H,s) 5.21 (1H,t J=4 Hz), 5.37 (2H,m), 6.88 (1H,d J=7 Hz), 6.99 (1H,t J=7 Hz), 7.2 (1H,m), 7.43 (1H,dd J=7,2 Hz).

(iii) A stirred solution of B (3.0 g), p-toluenesulphonic acid (20 mg) and 1,2,2-trimethoxyethane (10 ml) was heated at 90° C. for 3 hours. The cooled reaction mixture was diluted with ether (50 ml) and washed successively with 5% w/v sodium bicarbonate solution (3×20 ml), water (10 ml) and saturated brine (10 ml), then dried ($MgSO_4$) and evaporated. Flash chromatography of the residue, eluting with 15% v/v ethyl acetate/hexane, gave methyl 5(Z)-7-([2,4,5-cis]-2-methoxymethyl-4-o-methoxyphenyl-1,3-dioxan-5-yl)-heptenoate as a pale yellow oil (D) (2.50 g): NMR: 1.60 (3H,m), 1.83 (1H,m), 1.93 (2H, q J=7 Hz), 2.22 (2H,t J=7 Hz), 2.38 (1H,m), 3.46 (3H,s), 3.58 (2H,d J=4 Hz), 3.65 (3H,s), 3.80 (3H,s), 3.96 (1H,dm J=12 Hz), 4.09 (1H,dd J=12, 1Hz), 4.98 (1H,t J=4 Hz), 5.22 (1H,d J=2 Hz), 5.25 (2H,m), 6.83 (1H,br d J=7 Hz), 6.96 (1H,br t J=7 Hz), 7.24 (1H,td J=7, 1.5 Hz), 7.41 (1H, dd J=7,1.5 Hz).

(iv) 2M Potassium hydroxide solution (20 ml) was added to a stirred solution of D (2.50 g) in methanol (250 ml). After 20 hours, water (400 ml) was added. The mixture was washed with ether (100 ml), then acidified to pH4 with 2M hydrochloric acid and extracted with further ether (3×150 ml). The extracts were washed with saturated brine (2×50 ml), dried ($MgSO_4$) and evaporated. Flash chromatography of the residue, eluting with tolueneethyl acetateacetic acid (75:25: 0.2 v/v), gave 5(Z)-7-([2,4,5-cis]-2-methoxymethyl-4-o-methoxyphenyl-1,3-dioxan-5-yl)heptenoic acid, as a pale yellow oil (2.05 g): NMR: 1.60 (3H,m), 1.83 (1H,m), 1.97 (2H,m), 2.26 (2H,t J=7 Hz), 2.43 (1H,m), 3.46 (3H,s), 3.60 (2H,m), 3.80 (3H,s), 3.96 (1H, dm J=12 Hz), 4.09 (1H,dd J=12,1 Hz), 4.98 (1H,t J=5 Hz), 5.23 (1H,d J=2 Hz), 5.27 (2H,m), 6.84 (1H,dd J=7,1 Hz), 6.97 (1H,t d J=7,1 Hz), 7.23 (1H,td J=7,1.5 Hz), 7.40 (1H,dd J=7,1.5 Hz).

EXAMPLE 2

A solution of 4(Z)-6-([2,4,5-cis]-2-methoxymethyl-4-o-methoxyphenyl-1,3-dioxan-5-yl)hexenoic acid (740 mg) in dry DMPU (5 ml) was added to a stirred solution of sodium thioethoxide (1.008 g) in dry DMPU (25 ml) at 85° C. under argon. After 3 hours at 85° C., the reaction mixture was cooled to ambient temperature and poured into ice-water (150 ml). The aqueous mixture was washed with dichloromethane (3×100 ml), acidified to pH5 with 2M hydrochloric acid and extracted with ether (3×40 ml). These extracts were washed successively with water (15 ml) and saturated brine (15 ml), then dried ($MgSO_4$) and the solvent evaporated. Flash chromatography of the residue, eluting with toluene/ethyl acetate/acetic acid (70:30:0.2% v/v), gave 4-(Z)-6-([2,4,5-cis]-4-o-hydroxyphenyl-2-methoxymethyl-1,3-dioxan-5-yl)hexenoic acid as a yellow oil (329 mg), which crystallised slowly to give a solid of m.p. 103°–104° C.: NMR: 1.72 (1H,m), 1.90 (1H,m), 2.33 (4H,m), 2.67 (1H,m), 3.44 (3H,s), 3.59 (2H,d J=4 Hz), 3.94 (1H,dm J=12 Hz), 4.16 (1H,dd J=12,1 Hz), 4.93 (1H,t J=4 Hz), 5.26 (1H,d J=2 Hz), 5.27 (1H,m), 5.43 (1H,m), 6.89 (3H,m), 7.16 (1H,m): m/e 336 (M+).

The necessary starting material was obtained as follows:

(i) A solution of (4-o-methoxyphenyl-2,2-dimethyl-1,3-dioxan-cis-5-yl)acetaldehyde (15.8 g) in dry THF (75 ml) was added under argon to a stirred, ice-cooled solution of the yield prepared from (3-carboxypropyl)-triphenylphosphonium bromide (51.48 g) and potassium t-butoxide (26.88 g) in dry THF (400 ml). The mixture was stirred for 15 minutes at 4° C., then for 1.5 hours at ambient temperature and was then poured into ice-water (1 liter). The mixture obtained was washed with 50% v/v ether/hexane (2×250 ml) to remove the bulk of neutral material. The aqueous phase was acidified to pH 5 with acetic acid and extracted with ether (4×300 ml). These extracts were washed successively with water (3×150 ml), and saturated brine (2×100 ml), then dried (MgSO4) and evaporated. The residue was purified by flash chromatography, eluting with toluene-/ethyl acetate/acetic acid (80:20:2 v/v). The solid obtained was crystallised from 10% v/v ethyl acetate/-hexane (250 ml) to give 4(Z)-6-(4-o-methoxyphenyl-2,2-dimethyl-1,3-dioxan-cis-5-yl)hexenoic acid (A) (13.0 g), m.p. 99°–101° C.; NMR: 1.52 (3H, s), 1.54 (1H,m), 1.56 (3H,s), 1.80 (1H,m), 2.28 (4H,m), 2.49 (1H,m), 3.77 (1H,dd J=11,1 Hz), 3.82 (3H,s), 4.16 (1H,dm J=1 Hz), 5.28 (2H,m), 5.45 (1H,d J=2 Hz), 6.83 (1H,dd J=7,1 Hz), 6.97 (1H,td J=7,1 Hz), 7.22 (1H,td J=8,1 Hz), 7.48 (1H,dm J=8 Hz).

(ii) A solution of A (4.20 g) in a mixture of water (12 ml), 2M hydrochloric acid (0.5 ml) and THF (40 ml) was heated with stirring at 60°–70° C. After 2 hours the mixture was cooled to ambient temperature and poured into water (100 ml). The aqueous mixture was extracted with ether (3×50 ml). The combined extracts were washed successively with water (2×40 ml) and saturated brine (40 ml), then dried (MgSO4) and evaporated to give 4(Z)-ethythro-8 hydroxy-7-hydroxymethyl-8-o-methoxyphenyl-4-octenoic acid as a colourless oil (B) (3.80 g): NMR: 1.95 (1H,m), 2.11 (1H, m), 2.37 (5H,m), 3.67 (2H,m), 3.83 (3H,s), 4.84 (3H,br), 5.22 (1H,d J=4 Hz). 5.38 (2H,m), 6.88 (1H,br d J=7 Hz), 6.98 (1H,bt J=7 Hz), 7.25 (1H,td J=−7, 1.5 Hz), 7.42 (1H,dd J=7,1.5 Hz).

(iii) A solution of B (3.70 g) in ether (65 ml) was treated at 0°–4° C. with an ice-cold, ethereal solution of diazomethane until a yellow colour persisted. Acetic acid (0.2 ml) was then added and the solvent was evaporated. Flash chromatography of the residue, eluting with ethyl acetate/hexane (45:55 v/v), gave methyl 4(Z)-erythro-8-hydroxy-7-hydroxymethyl-8-o-methoxyphenyl-4-octenoate, as a colourless oil (C) (3.00 g): NMR: 1.90 (1H,m), 2.10 (1H,m), 2.36 (6H,m), 3.20 (1H,br), 3.66 (3H,s), 3.67 (2H,m), 3.83 (3H,s), 5.23 (1H,d J=5 Hz), 5.35 (2H,m), 6.87 (1H,br d J=8 Hz), 6.98 (1H,br t J=7 Hz), 7.24 (1H,td J=8,2 Hz), 7.45 (1H,dd J=7,2 Hz).

(iv) A stirred solution containing C (1.5 g), p-toluene-sulphonic acid (10 mg) and 1,1,2 trimethoxyethane (5 ml) was heated at 90° C. for 3 hours. The cooled reaction mixture was diluted with ether (50 ml) and successively washed with 5% w/v sodium bicarbonate solution (3×20 ml), water (10 ml), and saturated brine (10 ml), then dried (MgSO4) and evaporated. Flash chromatography of the residual oil, eluting with ethyl acetate/hexane (15:85 v/v) gave methyl 4(Z)-6-([2,4,5-cis]-2-methoxymethyl-4-o-methoxyphenyl-1, 3-dioxan-5-yl)hexenoate as a pale yellow oil (D) (865 mg); NMR: 1.60 (1H,m), 1.87 (1H,m ), 2.24 (4H,m ), 2.45 (1H,m ), 3.44 (3H,s ), 3.58 (2H,d J=4 Hz ), 3.64 (3H,s ), 3.80 (3H,s ), 3.96 (1H,d m J=12H z), 4.08 (1H,d d J=12, 1Hz), 4.98 (1H,t J=4 Hz ), 5.23 (1H,d J=2 Hz ), 5.27 (2H,m 6.83 (1H,b r d J=7 Hz ), 6.96 (1H,t d J=7,1 Hz), 7.23 (1H,t d J=7, 1.5 Hz ), 7.42 (1H,d d J=7, 1.5 Hz) .

(v) A stirred solution of D (865 mg) in methanol (70 ml) was hydrolysed at ambient temperature by reaction with 2M potassium hydroxide (7.0 ml) for 4 hours. Using a similar work-up procedure to that described in part (iv) of Example 1, there was obtained 4(Z)-6-([2,4,5-cis]-2-methoxymethyl-4-o-methoxyphenyl-1,3-dioxan-5-yl)hexenoic acid, as a colourless oil (740 mg); NMR: 1.60 (1H,m), 1.88 (1H,m), 2.27 (4H,m), 2.48 (1H,m), 3.44 (3H,s), 3.59 (2H, d J=4 Hz), 3.80 (3H,s), 3.96 (1H,dm J=12 Hz), 4.09 (1H,dd J=12,1 Hz), 4.98 (1H,t J=4 Hz), 5.23 (1H,d J-2 Hz), 5.29 (2H,m), 6.83 (1H,br d J=7 Hz), 6.96 (1H,td J=7,1 Hz), 7.23 (1H,td J=7,1.5 Hz), 7.42 (1H,dd J=7, 1.5 Hz).

EXAMPLE 3

A stirred solution of 4(Z)-6-([2,4,5-cis]-2-[2-ethoxyethyl]-4-o-methosyphenyl-1,3-dioxan-5-yl)hexenoic acid (A) (900 mg) in dry THF (3 ml) was treated at 4° C. under argon with a solution of lithium diphenylphosphide [prepared from chlorodiphenylphosphine (1.59 g) and lithium metal (202 mg) in dry THF (10 ml)]. The mixture was stirred for 5 minutes at 4° C., for 3 hours at 50° C., then cooled to 10° C. and added to ice-water (50 ml). The aqueous mixture was washed with ether (2×20 ml), acidified to pH5 with acetic acid and extracted with ether (3×30 ml). These extracts were washed successively with water (20 ml) and saturated brine (20 ml), then dried (MgSO4) and evaporated. Flash chromatography of the residue, eluting with toluene/ethyl acetate/acetic acid (75:25:0.2 v/v), gave 4(Z)-6-([2,4,5-cis]-2-[2-ethoxyethyl]-4-o-hydroxyphenyl-1,3-dioxan-5-yl)hexenoic acid, as a pale yellow oil (426 mg); NMR: 1.21 (3H,t J=7 Hz), 1.64 (1H,m), 1.88 (1H,m), 2.03 (2H,m), 2.33 (4H,m), 2.66 (1H,m), 3.51 (2H,q J=7 Hz), 3.60 (2H,m), 3.90 (1H,dm J=12 Hz), 4.09 (1H,dd J=12, 1.5 Hz), 4.92 (1H,t J=4.5 Hz), 5.20 (1H,d J=2 Hz), 5.28 (1H,m), 5.43 (1H,m), 6.87 (3H,m), 7.17 (1H,td J=7,1.5 Hz) m/e 382 (M+ +NH4), 365 (M+ +H).

The necessary starting material (A) was obtained using an analogous procedure to that described in Example 2, parts (iv) and (v). Thus, using the procedure of Ex.2 (iv) starting with 1,1,3-triethoxypropane instead of 1,1,2-trimethoxyethane, there was obtained methyl 4(Z)-6-([2,4,5-cis]-2-[2-ethoxyethyl]-4-o-methoxyphenyl-1,3-dioxan-5-yl)hexenoate in 62% yield as a pale yellow oil; NMR: 1.20 (3H,t J=7 Hz), 1.59 (1H,m), 1.84 (1H,m), 2.04 (2H,m), 2.26 (4H,m), 2.43 (1H,m), 3.49 (2H,q J=7 Hz), 3.61 (2H, t J=7 Hz), 3.64 (3H,s), 3.80 (3H,s), 3.92 (1H,dm J=12 Hz), 4.02 (1H,dd J=12,1 Hz), 4.92 (1H,t J=5 Hz), 5.18 (1H,d J=2 Hz), 5.25 (2H,m), 6.83 (1H,br d J=7 Hz), 6.97 (1H,dd J=7,1 Hz), 7.23 (1H,td J=7,1.5 Hz), 7.43 (1H,td J=7,1.5 Hz). This ester was then hydrolysed using the procedure of Ex.2(v) to give the required acid (A) as a colourless oil in 95% yield; NMR: 1.18 (3H,t J=7 Hz), 1.57 (1H,m), 1.85 (1H,m), 2.02 (2H,m), 2.27 (4H,m), 2.47 (1H,m), 3.48 (2H,q J=7 Hz), 3.61 (2H,t J=7 Hz), 3.80 (3H,s), 3.91 (1H,dm J=12 Hz), 4.03 (1H,br d J=12 Hz), 4.92 (1H,t J=5 Hz), 5.18 (1H,d J=2 Hz), 5.29 (2H,m), 6.83 (1H,br d J=7 Hz), 6.97 (1H, br t J=7 Hz), 7.23 (1H,t d J=7,1.5 Hz), 7.43 (1H,dd J=7,1.5 Hz).

EXAMPLE 4

A stirred solution of 4(Z)-6-([2,4,5-cis]-2-cyclohexyloxymethyl-4-o-methoxyphenyl-1,3-dioxan-5-yl)hexenoic acid (0.50 g) in dry THF (3 ml) was treated at 4° C. under argon with a solution of lithium diphenylphosphide prepared from chlorophenylphosphine (0.99 g) and lithium metal (0.13 g) in dry THF (5 ml)]. The mixture was stirred 5 minutes at 4° C., then for 3 hours at 50° C., cooled to 10° C. and added to ice-water (50 ml). The aqueous mixture was washed with ether (3×20 ml), acidified to pH5 with acetic acid and extracted with ether (3×25 ml). These extracts were washed successively with water (3×20 ml) and saturated brine (20 ml), then dried (MgSO$_4$) and evaporated. The residue was purified by MPLC, eluting with hexaneethyl acetated acetic acid (80:20:1 v/v), to give 4(Z)-6([2,4,5-cis]-2-cyclohexyloxymethyl-4-o-hydroxyphenyl-1,3-dioxan-5-yl) hexenoic acid as a clear oil which slowly crystallised to give solid (0.44 g) of m.p. 91°–93° C.: NMR: 1.28 (5H,m), 1.52 (1H,m), 1.73 (3H,m), 1.92 (3H,m), 2.32 (4H,m), 2.66 (1H,m), 3.33 (1H,m), 3.65 (2H,d J=4 Hz), 3.92 (1H,dm J=1 Hz), 4.14 (1H,dd J=11,1 Hz), 4.92 (1H,t =4 Hz), 5.26 (1H,d J=2 Hz), 5.27 (1H,m), 5.44 (1H,m), 6.88 (3H,m), 7.16 (1H, td J=7,1.5 Hz), 8.50 (2H,br); m/e 422 (M$^+$+NH$^4$), 405 (M$^+$+H).

The necessary starting materials were prepared as follows:

(i) Cyclohexanol (11.00 g) was added slowly over 2 hours to a stirred suspension of sodium hydride (4.80 g, 50% w/w dispersion in oil) in dry DMPU (100 ml) at 50° C. under argon. The mixture was stirred for an additional 30 minutes, then cooled to 5° C. and treated with 2 -bromo-1,1-dimethoxyethane (16.9 g). Stirring was continued for 18 hours at ambient temperature. The mixture was then poured into ice-water (250 ml). The aqueous mixture was extracted with ether (4×100 ml). The combined extracts were washed successively with water (3×100 ml) and saturated brine (100 ml), then dried (MgSO$_4$) and evaporated. Flash chromatography of the residue, eluting successively with hexane, 5% v/v ethyl acetate hexane and 10% v/v ethyl acetate/hexane, gave 2-cyclohexylox-1,1-dimethoxyethane as an oil (A) (7.32 g). This was used without further purification. [A sample was distilled under vacuum (bulb to bulb transfer); NMR: 1.29 (5H,m), 1.55 (1H,m), 1.76 (2H,m), 1.92 (2H,m), 3.27 (1H,m), 3.40 (6H,s), 3.50 (2H,d J=5 Hz), 4.48 (1H,t J=5 Hz).]

(ii) A stirred mixture of 4-(Z)-erythro-8-hydroxy-7-hydroxymethyl-8-methoxyphenyl-4-octenoic acid (1.40 g), p-toluenesulphonic acid (5 mg) and A (5.40 g) was heated at 100° C. for 4 hours. The solution was cooled, methanol (10 ml) added and the mixture stirred for 18 hours at ambient temperature. Triethylamine (1.40 g) was added and the solvent evaporated. The residue was purified by MPLC, eluting with 15% v/v ethyl acetate/hexane, to give methyl 4(Z)-6-([2,4,5-cis]-2-cyclohexyloxymethyl-4-o-methoxyphenyl-1,3-dioxan-5-yl)hexenoate as an oil (B) (0.97 g).

(iii) A solution of the ester B (0.97 g) in methanol (50 ml) was hydrolysed using 2M potassium hydroxide (7 ml) for 18 hours in accordance with the general procedure described in Example 2

(v). There was thus obtained, following MPLC of the crude product eluting with hexaneethyl acetate/acetic acid (75:25:1 v/v)4(Z)-6-([2,4,5-cis]-2-cyclohexyloxymethyl-4-o-methoxyphenyl-1,3-dioxan-5-1)hexenoic acid, as a clear oil (0.72 g); NMR: 1.26 (5H,m), 1.63 (4H,m), 1.94 (3H,m), 2.27 (4H,m), 2.47 (1H,m), 3.34 (1H,m), 3.66 (2H,d J=4 Hz), 3.80 (3H,s), 3.95 (1H,dm J=11 Hz), 4.08 (1H,br d J=12 Hz), 4.94 (1H,t J=4 Hz), 5.21 (1H,d J=2 Hz), 5.27 (2H,m), 6.83 (1H,br d J=7), 6.96 (1H, br t J=7 Hz), 7.23 (1H,td J=7,1.5 Hz), 7.40 (1H, dd J=7,1 Hz).

EXAMPLE 5

Using a similar procedure to that described in Example 4, but starting from 4(Z)-6-([2,4,5-cis]-4-o-methoxyphenyl-2-phenoxymethyl-1,3-dioxan-5-yl)hexenoic acid, there was obtained 4(Z)-6-([2,4,5-cis]-4-o-hydroxyphenyl-2-phenoxymethyl-1,3-dioxan-5-yl)hexenoic acid as a sticky solid in 75% yield: NMR: 1.77 (1H,m), 1.92 (1H,m), 2.31 (4H,m), 2.68 (1H,m), 4.00 (1H,dm J=11 Hz), 4.16 (2H,d J=4 Hz), 4.19 (1H,br d J=11 Hz), 5.16 (1H, t J=4 Hz), 5.31 (1H,d J=2 Hz), 5.36 (2H,m), 6.50 (1H,6). 6.92 (6H,m), 7.16 (1H,td J=7,1.5 Hz). 7.29 (2H,m); m/e 398 (M$^+$).

The starting material was obtained as follows:

A mixture of 4(Z)-erythro-8-hydroxy-7-hydroxymethyl-8-o-methoxyphenyl-4-octenoic acid (792 mg), p-toluene sulphonic acid (5 mg) and 2-phenoxy-1,2-dimethoxyethane (2.72 g) was stirred at 80° C. for 3 hours. The mixture was cooled and diluted with ether (25 ml) and then extracted with 0.2M sodium hydroxide (3×15 ml). The aqueous extracts were acidified to pH5 with acetic acid and extracted with ether (3×20 ml). These extracts were washed successively with water (2×15 ml) and saturated brine (15 ml), then dried (MgSO$_4$) and evaporated. The residue was purified by MPLC, eluting with hexan/ethyl acetate/acetic acid (75:25:1 v/v), to give 4(Z)-6-([2,4,5,cis]-4-o-methoxyphenyl-2-phenoxymethyl-1,3-dioxan-5-yl)hexenoic acid, as a clear oil (229 mg); NMR: 1.63 (1H, m), 1.90 (1H,m), 2.29 (4H,m), 2.50 (1H,m), 3.81 (3H,s), 4.00 (1H,dm J=11 Hz), 4.22 (1H,br d J=11 Hz), 4.17 (2H,d J=4 Hz), 5.18 (1H,t J=4 Hz), 5.28 (1H,d J=2 Hz), 5.31 (2H,m), 6.91 (5 H,m), 7.25 (3H,m), 7.41 (1H,dd J=7,1.5 Hz).

EXAMPLE 6

A stirred solution of 4(Z)-6-([2,4,5-cis]-2 -[1-methyl-1-phenoxyethyl]-4-o-methoxyphenyl-1,3-dioxan-5-yl)hexenoic acid (584 mg) in dry (THF) (5 ml) was treated at 4° C. under argon with a solution of lithium diphenylphosphide [prepared from chlorodiphenylphosphine (1.44 ml) and lithium metal (224 mg) in dry THF (8 ml)]. The mixture was stirred for 5 minutes at 4° C., then for 3.5 hours at 55° C., cooled to 1020 C. and added to ice-water (100 ml). The aqueous solution was washed with ether (2×50 ml), acidified to pH5 with acetic acid and extracted with ether (3×50 ml). These extracts were washed successively with water (2×50 ml) and saturated brine (50 ml), then dried (MgSO$_4$) and evaporated. The residue was purified by MPLC, eluting with hexan/ethyl acetateacetic acid (85:15:1 v/v), to give 4(Z) 6 ([2,4,5 cis]4-o-hydroxyphenyl-2-[1-methyl-1-phenoxyethyl]-1,3-dioxan-5-yl)hexenoic acid as a clear oil (426 mg); NMR (90 MHz): 1.36 (6H,bs), 1.88 (2H,m), 2.36 (4H,m), 2.68 (1H,m), 3.96 (1H,dm J=11 Hz), 4.23 (1H,bd J=11 Hz), 4.80 (1H,s), 5.33 (1H,d J=2 Hz), 5.38 (2H,m), 7.06 (9H,m), 8.50 (2H,b); m/e 444 (M+ +NH$_4$), 427 (M+ +H).

The starting material was obtained as follows:

A suspension of 4(Z)-6-(4-o-methoxyphenyl-2,2-dimethyl-1,3-dioxan-cis-5-yl)hexenoic acid (1.5 g) in 2-methyl-2-phenoxypropionaldehyde (3.0 g) containing p-toluenesulphonic acid (10 mg) was stirred for 18 hours at ambient temperature and then heated at 60° C. for 6 hours. The cooled solution was diluted with ether (30 ml) and extacted with 0.5M sodium hydroxide solution (3×10 ml). The aqueous extracts were washed with ether (20 ml), then acidified to pH5 with acetic acid and extracted with ether (3×15 ml). These extracts were washed successively with water (2×10 ml) and saturated brine (10 ml), then dried (MgSO$_4$) and evaporated. The residue was purified by MPLC, eluting with hexane/ethyl acetate/acetic acid (85:15:1 v/v), to give 4(Z)-6-([2,4,5-cis]-2-[1-methyl-1-phenoxyethyl]-4-o-methoxyphenyl-1,3-dioxan-5-yl)hexenoic acid as a clear oil (655 mg); NMR: 1.34 (3H,s) 1.42 (3H,s), 1.57 (1H,m), 1.89 (1H,m), 2.30 (4H,m), 2.49 (1H,m), 3.81 (3H,s), 3.98 (1H, dm J=11 Hz), 4.15 (1H, dd J=11,1 Hz), 4.80 (1H,s), 5.24 (1H, d J=2 Hz), 5.32 (2H,m), 6.85 (1H,ddJ=7,1 Hz), 7.03 (4H,m), 7.24 (3H,m), 7.43 (1H,dd J=7,1.5 Hz): m/e 458 (M+ +NH$_4$), 441 (M+ +H)

The necessary 2-methyl-2-phenoxypropionaldehyde was itself obtained as follows:

A stirred solution of methyl 2-methyl-2-phenoxypropionate (3.88 g) in dichloromethane (100 ml) was treated dropwise at −70° C. under argon, with a 1M solution of diisobutylaluminium hydride (dibal) in dichloromethane (21 ml). The solution was stirred for 1 hour at −70° C., then allowed to warm to −30° C., after which it was poured into a vigorously stirred aqueous solution of potassium sodium tartrate tetrahydrate (50 g) dissolved in water (100 ml) cooled to 4° C. After stirring for 30 minutes, the mixture was separated by filtration through diatomaceous earth. The filtrate was extracted with ether (4×100 ml) and the extracts were washed with saturated brine (2×100 ml), dried (MgSO$_4$) and evaporated. The residual oil (3.18 g) containing 2-methyl-2-phenoxypropionaldehyde was used without further purification.

EXAMPLE 7

A stirred solution of 4(Z)-6-([2,4,5-cis]-2-[1-methyl-1-propoxyethyl]-4-o-methoxyphenyl-1,3-dioxan-5-yl)hexenoic acid (803 mg) in dry THF (2 ml) was treated at 4° C. under argon with a solution of lithium diphenylphosphide [prepared from chlorodiphenylphosphine (1.80 ml) and lithium metal (280 mg) in dry THF (10 ml)]. The mixture was stirred for 5 minutes at 4° C., then for 3 hours at 50° C. cooled to 10° C. and added to icewater (50 ml). The aqueous solution was washed with ether/hexane (1:1 v/v) (3×25 ml), acidified to pH5 with acetic acid and extracted with ether (3×25 ml). These extracts were washed successively with water (2×25 ml) and saturated brine (25 ml), dried (MgSO$_4$) and evaporated. The residue was purified by MPLC, eluting with hexan/ethyl acetateacetic acid (85:15:1 v/v), to give 4(Z)-6-([2,4,5-cis]-4-o-hydroxyphenyl-2-[1-methyl-1-propoxyethyl]1,3-dioxan-5-yl)hexenoic acid as a colourless oil *(650 mg); MMR: 0.90 (3H,t J=7 Hz), 1.25 (3H,s), 1.26 (3H,s), 1.57 (2H,q J=7 Hz), 1.72 (1H,m), 1.92 (1H,m), 2.33 (4H,m), 2.63 (1H,m), 3.41 (2H, td J=7,1 Hz), 3.88 (1H,dm J=11 Hz), 4.15 (1H,dd J=11,1 Hz), 4.59 (1H,s), 5.25 (1H,d J=2 Hz), 5.38 (2H,m), 6.87 (3H,m), 7.16 (1H,td J 7,1.5 Hz); M/e 39Z (M+). [*The oil crystallised slowly to give solid, m.p. 62°–63° C. (recrystallised from ethyl acetate/hexane)].

The necessary starting material was obtained as follows:

A suspension of 4(Z)-6-(4-o-methoxyphenyl-2,2-dimethyl-1,3-dioxan-cis-5-yl)hexenoic acid (1.5 g) in 2-methyl-2-propoxypropionaldehyde (4 g) containing p-toluenesulphonic acid (10 mg) was stirred for 18 hours. The solution obtained was diluted with ether (25 ml) and extracted with 0.2M sodium hydroxide solution (3×25 ml). The aqueous extracts were acidified to pH5 with acetic acid and extracted with ether (3×25 ml). These extracts were washed successively with water (2×25 ml) and saturated brine (25 ml), then dried (MgSO$_4$) and evaporated. The residue was purified by MPLC, eluting with hexan/ethyl acetateacetic acid (80:20:1 v/v) to give 4(Z)-6-([2,4,5-cis]-2-[1-methyl-1-propoxyethyl]-4-o-methoxyphenyl-1,3-dioxan-5-yl)hexenoic acid as a clear oil (1.01 g); NMR: 0.88 (3H,t J=7 Hz), 1.27 (3H,s), 1.30 (3H,s), 1.54 (2H,q J=7 Hz), 1.55 (1H,m), 1.84 (1H,m), 2.28 (4H,m), 2.43 (1H,m), 3.46 (2H, t J=7 Hz), 3.80 3H,s) 3.90 (1H,dm J=11Hz), 4.09 (1H, dd J=11Hz), 4.64 1H,s). 5.19 (1H,d J=2 Hz), 5.28 (2H,m), 6.84 (1H,dd J=7,1 Hz), 6.97 (1H,td J=7,1 Hz), 7.24 (1H,td J=7,1.5 Hz), 7.42 (1H,dd J=7,1.5 Hz): m/e (-VE FAB) 405 (M-H)−.

The 2-methyl-2-propoxypropionaldehyde required as starting material was obtained as a clear oil (4.0 g) in an analogous manner to that described in Example 1 (a) for 2-methyl-2-phenoxypropionaldehyde but starting from the known compound methyl 2-methyl-2-propoxypropionate (3.8 g).

EXAMPLE 8

Using a similar procedure to that described in Example 4, but starting from 4(Z)-6-([2,4,5-cis]-4-o-methoxyphenyl-2-[1-butoxyethyl]-1,3-dioxan-5-yl)hexenoic acid, there was obtained 4(Z)-6-([2,4,5-cis]-4-o-hydroxyphenyl-2-[1-butoxyethyl]-1,3-dioxan-5-yl)hexenoic acid as a clear oil in 92% yield; NMR: 0.91 (3H, t J=7 Hz), 1.24 (4H, m), 1.38 (1H, m), 1.56 (2H, m), 1.69 (1H, m), 1.90 (1H, m), 2.33 (4H, m), 2.66 (1H, m), 3.55 (3H, m), 3.90 (1H dm J=12 Hz), 4.15 (1H, d) J=11Hz), 4.73 (1H, 2d J=3 Hz), 5.24 (1H, d J=2 Hz), 5.35 (2H, m), 6.88 (3H, m), 7.17.(1H, m), 8.10 (1H, bs); m/e 393 (M+ +H).

The necessary starting materials was obtained as follows:

(i) Sodium borohydride (2.84 g) was added portionwise over 30 minutes to a stirred solution of 3-ketobutyraldehyde dimethyl acetal (18.0 ml) in absolute ethanol (75 ml), the temperature being maintained at 20°–25° C. with water cooling. The mixture was stirred for a further 2 hours at ambient temperature was then poured into saturated ammonium chloride. The subsequent mixture was extracted with ether (3×100 ml). The extracts were washed with saturated brine (50 ml), dried (MgSO$_4$) and the solvent evaporated to give 1,1-dimethoxy-2-propanol (A) as a yellow oil: NMR (90 MHz): 1.20 (3H, d J=6 Hz), 2.30 (1H, bs), 3.42 (3H, s), 3.47 (3H, s), 3.75 (1H, m), 4.08 (1H, d J=6 Hz).

(ii) A solution of A (3.75 g in DMPU (2 ml) was added dropwise under argon to a stirred suspension of sodium hydride (0.75 g) in DHPU (25 ml). The mixture was heated to 50° C. for 30 minutes, then cooled to 10° C. and butyl bromide (3.7 ml) added. Stirring was continued overnight and then water (100 ml) was added. The mixture was extracted with ether (3×50 ml). The extracts were washed with water (50 ml), brine (50 ml), dried (Mg SO₄) and the solvent evaporated. The residue was purified by flash chromatography, eluting with 10% v/v ethyl acetate/hexane to give 1,1-dimethoxy-2-butoxy propane (B) as a clear oil (1.8 g); NMR (90 MHz): 0.8–1.8 (10H, m), 3.50 (9H, m), 4.15 (1H, d J=5 Hz).

(iii) Using a similar procedure to that described in Example 4(ii) and (iii), but starting from 1,1-dimethoxy-2-butoxypropane (B), there was obtained 4(Z)-6-([2,4,5-cis]-4-o-methoxyphenyl-2-[1-butoxyethyl]-1,3-dioxane-5-yl)hexenoic acid, as a clear oil in 49% yield: NMR: 0.91 (3H, m), 1.28 (3H, t J=6 Hz), 1.35 (2H, m), 1.57 (3H, m), 1.85 (1H, m), 2.36 (5H, m), 3.58 (3H, m), 3.80 (3H, s), 3.93 (1H, dm J=11 Hz), 4.09 (1H, bd J=11Hz), 4.73 (0.5H, d J=3 Hz), 4.83 (0.5H, d J=3 Hz), 5.29 (3H, m), 6.84 (1H, d J=7 Hz), 6.97 (1H, t J=7 Hz), 7.24 (1H, bt J=7 Hz), 7.42 (1H, m): m/e 406 (M+).

EXAMPLE 9

Using a similar procedure to that described in Example 6, but starting from (-) 4(Z)-6-([2,4,5-cis]-2-[1-methyl-1-phenoxyethyl]-4-o-methoxyphenyl-1,3-dioxan-5-yl)hexenoic acid (A), there was obtained (-)-4-(Z)-6-([2,45-cis]-4-o-hydroxyphenyl-2-[1-methyl-1-phenoxyethyl]-1,3-dioxan-5-yl)hexenoic acid in 64% yield as a colourless oil: NMR essentially the same as for the racemate (Example 6): m/e 427(M+ +H); $^{20}[\alpha]_D$-129.9° (c, 0.85: methanol).

The starting material A was obtained as follows: (i) Solid potassium t-butoxide (4.48 g) was added under argon to a stirred, ice-cooled mixture of (3-carboxypropyl)triphenylphosphonium bromide (6.44 g) and (-)-[2,3-trans]-tetrahydro-5-hydroxy 3-hydroxymethyl-2-o-methoxyphenylfuran (B) (2.24 g) in dry THF (75 ml). The mixture was stirred for 15 minutes at 4° C., then for 1 hour at ambient temperature and was then poured into ice-water (150 ml). The mixture obtained was washed with ether (2×50 ml) to remove the bulk of the neutral material. The aqueous phase was acidified to pH4 with 1M hydrochloric acid and extracted with ether (1×100 ml, 2×50 ml). These combined extracts were washed successively with water (2×50 ml) and saturated brine (2×50 ml), then dried (MgSO₄) and evaporated. The residue was purified by flash chromatography, eluting with ether/hexane/acetic acid (80:20:1 v/v) to give (-) erythro-4(Z)-8-hydroxy-7-hydroxymethyl-8-o-methoxyphenyl-4-octenoic acid (C) as a colourless oil (2.76 g): $^{22}[\alpha]_D$-68.3° (c 1.1, methanol); NMR: 1.92 (1H,m), 2.0–2.6 (6H,m), 3.67 (2H,m), 3.82 (3H,s), 5.21 (1H,d J=5 Hz), 5.37 (2H,m), 6.87 (1H,dd J=8,1 Hz), 6.98 (1H,td J=7,1 Hz), 7.25 (1H,m), 7.42 (1H,dd J=7,1 Hz): m/e 294 (M+). (ii) A solution of C (2.57 g) in 2,2-dimethoxypropane (8.5 ml) was treated with 'Amberlyst'-15 (Trademark of Rohm and Haas Company) strongly acid, macroreticular ion-exchange resin (0.5 g) and the mixture stirred for 2½ hours at ambient temperature. The solid was removed by filtration and washed with ether (10 ml). The filtrate and washings were concentrated in vacuo and the residue was purified by MPLC, eluting with hexan/ethyl acetate/ acetic acid (80:20:1 v/v). A clear oil was obtained which slowly crystallised to give (-)4(Z)-6-(4-o-methoxyphenyl-2,2-dimethyl-1,3-dioxan-cis-5-yl)hexenoic acid (D) (2.48 g). Recrystallisation from hexane gave solid of m.p. 71°–73° C., $^{23}[\alpha]_D$—145.5° (c 1.1, methanol) with an NMR spectrum essentially the same as that of the corresponding racemate (Compound A in Ex.1).

(iii) The hexenoic acid D was reacted with 2-methyl-2-phenoxypropionaldehyde using the same procedure as described for the corresponding racemate in Example 6. There was thus obtained (-)-4-(Z)-6-([2,4,5-cis]-2-[1-methyl-1-phenoxyethyl]-4-o-methoxyphenyl-1,3-dioxan-5-yl)hexenoic acid as a colourless oil in 21% yield, having an NMR spectrum essentially the same as that of the racemic starting material described in Example 6.

The furan derivative B was itself obtained as follows:

(iv) Succinic anhydride (22 g), o-methoxybenzaldehyde (20 g) and anhydrous zinc chloride (44 g) were added to dichloromethane (dried over alumina, 200 ml) and the mixture stirred under argon. Triethylamine (41 ml) was added to the ice-cooled mixture over a period of 20 minutes. The reaction mixture was then stirred at 20°–25° C. for 18 hours, after which time hydrochloric acid (2M,130 ml) and ethyl acetate (200 ml) were added. The subsequent mixture was stirred for 5 minutes. The aqueous phase was separated and extracted with ethyl acetate (150 ml) The combined extracts were washed with saturated brine (50 ml) and then extracted with saturated sodium bicarbonate solution (3×200 ml). The combined aqueous extracts were washed with ethyl acetate, and then acidified to pH2 with concentrated hydrochloric acid. The oil which separated was extracted into ethyl acetate (2×150 ml). The combined extracts were washed with saturated brine (4×50 ml)until acid free, then dried (MgSO₄) and evaporated. Toluene (300 ml) was added to the residue and the mixture was distilled atmospheric pressure until the residual material attained 110° C. On cooling to 20° C., tetrahydro-2-o methoxyphenyl-5 oxo-3 furancarboxylic acid separated as a crystalline white solid (27.2 g, 78%) (m.p. 106° C.) which was shown by NMR to be a mixture of [2,3 cis-]-and [2,3-trans]-isomer: 2.8 3.0 (2H,m), 3.1–3.6 (1H,m), 3.8 (3H,s), 5.82 (0.75 H,d) [trans], 5.95 (0.25 H, d) [cis], 6.8–7.5 (4H,m).

(v) A mixture of [2,3-cis] and [2,3-trans]tetrahydro-2-o-methoxyphenyl-5-oxo-3-furancarboxylic acid (188.6 g) was added to an ice cooled solution of concentrated sulphuric acid (320 ml) in water (480 ml) and stirred at 20°–25° C. for 18 hours. Water (800 ml) was then added and the mixture extracted with ethyl acetate (2×750 ml). The combined extracts were washed with brine (4×500 ml) until acid free, dried (MgSO₄) and evaporated to low volume. Toluene (1 liter) was added and the distillation continued at atmospheric pressure until the residual material attained a temperature of 110° C. On cooling pure [2,3 trans]-tetrahydro-2-methoxyphenyl- 5-oxo-3-furan-carboxylic acid separated as a white crystalline solid (169.5 g,90%), m.p. 133°–134° C.: NMR: 2.8–3.0 (2H,d), 3.3–3.6 (1H,m), 3.8 (3H,s), 5.82 (1H,d), 6.8–7.4 (4H,m).

(vi) A solution of d-ephedrine (61.2 g) in hot ethyl acetate (150 ml) was added to a solution of [2,3-trans]-tetrahydro-2-o-methoxyphenyl-5-oxo-3-furancarboxylic acid (87.6 g) in hot ethyl acetate (350 ml). The mixture was allowed to cool to room temperature during 2 hours and the crystalline salt which had formed was separated by filtration to give 62 g of solid material having $^{25}[\alpha]_D$+40.2° (methanol). This material was recrystallised twice from ethyl acetate to give 48 g of optically pure solid $^{25}[\alpha]_D + 50.3°$ (methanol). This solid was added to ethyl acetate (1 liter) and 2M hydrochloric acid (150 ml). The ethyl acetate layer was washed with brine (2×100 ml) until the pH of the washings was pH2-3, and then dried (MgSO$_4$) and evaporated. The residue was dissolved in boiling toluene (200 ml). Insoluble material was removed by hot filtration. The filtrate was allowed to cool to give (+)-[2,3-trans]-tetrahydro-2-o-methoxyphenyl-5-oxo-3-furancarboxylic acid (E) (27.4 g) $^{25}[\alpha]_D + 33.0°$ (methanol). Recrystallisation from toluene gave material of $^{25}[\alpha]_D + 33.8°$ (methanol), m.p. 125°-127° C. (decomposition), shown to be >98% optically pure by conversion of a small sample to its (−) amyl ester and examination of the $^{13}$C NMR spectrum.

(vii) A solution of E (97.5 g) in dry tetrahydrofuran (150 ml) was cooled to 15° C. and treated with a solution of borane in tetrahydrofuran (500 ml) of a 1M solution) with the temperature maintained at 20°-25° C. After 30 minutes the reaction was complete (as judged by TLC analysis) and water (200 ml) was added slowly to decompose the excess borane. The mixture was concentrated in vacuo and the residue was mixed with ethyl acetate (500 ml). The organic layer was washed successively with saturated potassium carbonate solution (2×100 ml) and saturated brine, dried (MgSO$_4$), and evaporated to give [4,5-trans]-tetrahydro-4-hydroxymethyl-5-o-methoxyphenylfuran-2-one (F) as a viscous oil (81.8 g, having $^{25}[\alpha]_D$-14.2° (methanol) and a satisfactory NMR spectrum (d$_6$ acetone): 2.6 (3H,m), 3.7 (2H,m), 3.8 (3H,s), 4.1 (1H,br), 5.55 (1H,m), 6.8-7.5 (4H,m).

(viii) A solution of F (obtained above) in 1,2-dimethoxyethane (150 ml) and dry toluene (500 ml) was cooled under a nitrogen atmosphere to −60° C. A toluene solution of diisobutylaluminium hydride (672 ml of 1.23M solution) was then added slowly. After 30 minutes the reaction was quenched by addition of methanol (50 ml) and the mixture allowed to warm up to room temperature. 2M Hydrochloric acid (1 liter) and ethyl acetate (500 ml) were then added and the mixture stirred. The aqueous phase was separated and extracted with ethyl acetate (2×500 ml). The ethyl acetate phase and extracts were combined, dried (MgSO$_4$) and evaporated. The residual oil was dissolved in hot toluene (500 ml). The solution obtained gave on cooling (−)-[2,3-trans]-tetrahydro-5-hydroxy-3-hydroxymethyl-2-o-methoxyphenylfuran methoxyphenylfuran (B) as a white solid (63.3 g), $^{25}[\alpha]_D$−24.2° (methanol), m.p. 110°-111° C.; NMR: 1.5-2.4 (3H,m), 3.4-4.0 (2H,m), 3.8 (3H,s), 4.2-4.8 (2H,br), 5.25 (1H, m), 5.6 (1H, m), 6.9-7.9 (4H, m).

EXAMPLE 10

Illustrative pharmaceutical dosage forms of the invention include the following tablet, capsule and aerosol formulations, which may be obtained by conventional procedures well known in the art of pharmacy and are suitable for therapeutic or prophylactic use in humans:

| (a) Tablet I | mg/tablet |
|---|---|
| Compound X* | 1.0 |
| Compound Y* | 1.0 |
| Lactose Ph. Eur. | 92.25 |
| Croscarmellose sodium | 4.0 |
| Maize starch paste (5% w/v aqueous paste) | 0.75 |
| Magnesium stearate | 1.0 |

| (b) Tablet II | mg/tablet |
|---|---|
| Compound X* | 5.0 |
| Compound Y* | 50.0 |
| Lactose Ph. Eur | 218.75 |
| Croscarmellose sodium | 6.0 |
| Maize starch | 15.0 |
| Polyvinylpyrrolidone (5% w/v aqueous paste) | 2.25 |
| Magnesium stearate | 3.0 |

| (c) Tablet III | mg/tablet |
|---|---|
| Compound X* | 25 |
| Compound Y* | 75 |
| Lactose Ph. Eur. | 182.75 |
| Croscarmellose sodium | 12.0 |
| Maize starch paste (5% w/v aqueous paste) | 2.25 |
| Magnesium stearate | 3.0 |

| (d) Capsule I | mg/capsule |
|---|---|
| Compound X* | 5 |
| Compound Y* | 5 |
| Lactose Ph. Eur. | 488.5 |
| Magnesium stearate | 1.5 |

| (e) Capsule II | mg/ml |
|---|---|
| Compound X* | 50 |
| Compound Y* | 250 |
| Lactose Ph. Eur | 199 |
| Magnesium stearate | 1 |

| (f) Aerosol I | mg/ml |
|---|---|
| Compound X* | 5.0 |
| Compound Y* | 5.0 |
| Sorbitan trioleate | 13.5 |
| Trichlorofluoromethane | 910.0 |
| Dichlorodifluoromethane | 490.0 |

| (g) Aerosol II | mg/ml |
|---|---|
| Compound X* | 0.1 |
| Compound Y* | 0.1 |
| Sorbitan trioleate | 0.27 |
| Trichlorofluoromethane | 70.0 |
| Dichlorodifluoromethane | 280.0 |
| Dichlorotetrafluoroethane | 1094.0 |

| (h) Aerosol III | mg/ml |
|---|---|
| Compound X* | 1.0 |
| Compound Y* | 2.0 |
| Sorbitan trioleate | 3.38 |
| Trichlorofluoromethane | 67.0 |
| Dichlorodifluoromethane | 1086.0 |
| Dichlorotetrafluoroethane | 191.6 |

| (i) Aerosol IV | mg/ml |
|---|---|
| Compound X* | 1.5 |
| Compound Y* | 2.0 |
| Soya lecithin | 2.7 |
| Trichlorofluoromethane | 67.5 |
| Dichlorodifluoromethane | 1086.0 |
| Dichlorotetrafluoroethane | 191.6 |

Note
*Compound X is a compound of formula I, or a pharmaceutically acceptable salt thereof, for example a compound of formula I described in any preceding Examples, typically Ex. 6 or 9.
*Compound Y is a TXA$_2$ synthetase inhibitor, or a pharmaceutically acceptable salt thereof, for example as specified hereinbefore e.g. dazoxiben, or the compound known as CV4151, or a salt thereof.

The tablet compositions (a)-(c) may be enteric coated by conventional means, for example to provide a coating of cellulose acetate phthalate. The aerosol compositions (e)-(h) may be used in conjunction with standard, metered dose aerosol dispensers, and the suspending agents sorbitan trioleate and soya lecithin may be replaced by an alternative suspending agent such as sorbitan monooleate, sorbitan sesquioleate. polysorbate 80, polyglycerol oleate or oleic acid. Other formulations containing different amounts of the active ingredients X and Y may be obtained using generally analogous procedures and excipients well known in the pharmceutical art.
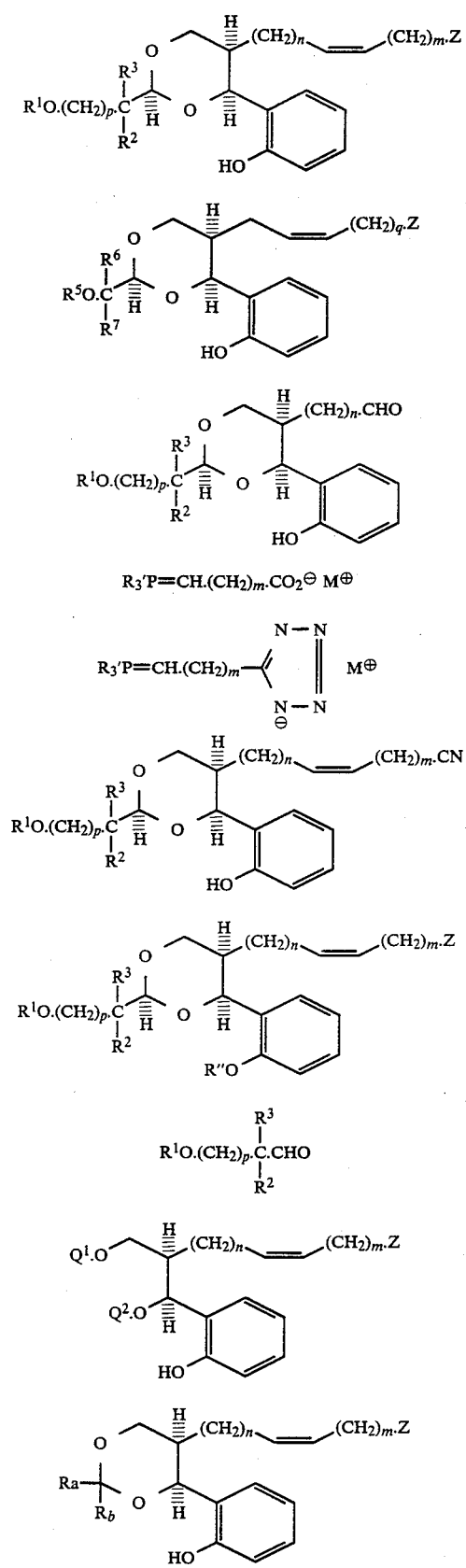
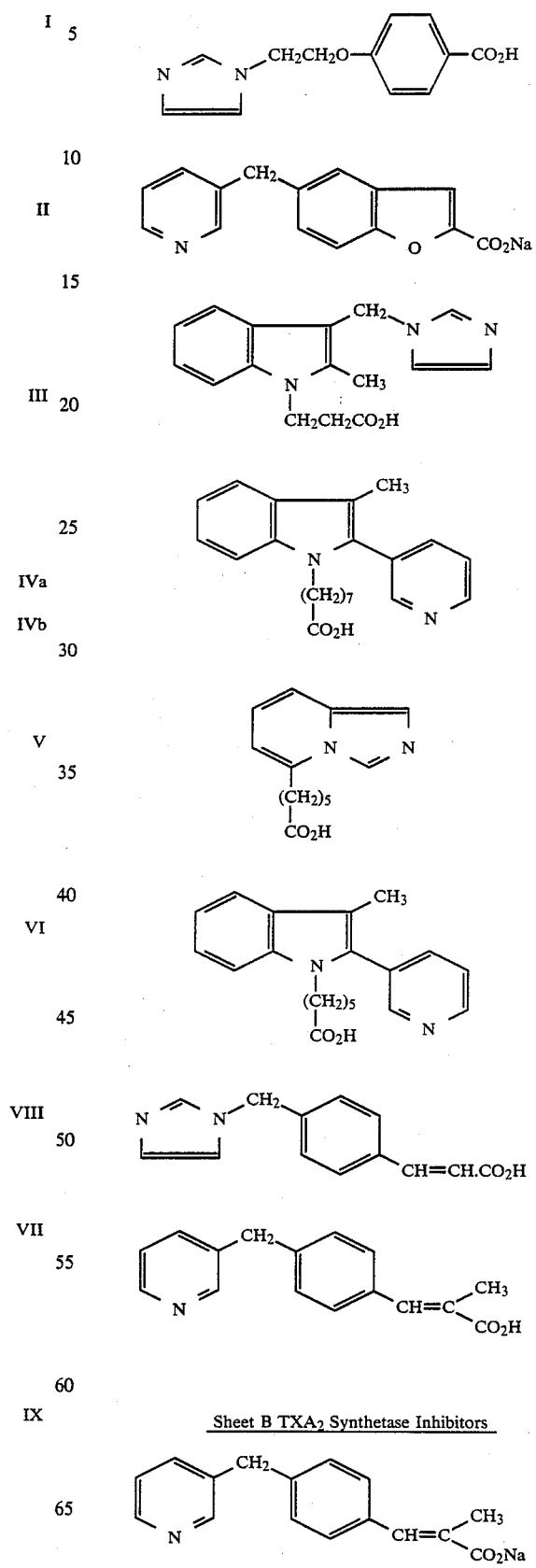
Sheet A TXA$_2$ Synthetase Inhibitors
Sheet B TXA$_2$ Synthetase Inhibitors -continued
Sheet B TXA₂ Synthetase Inhibitors

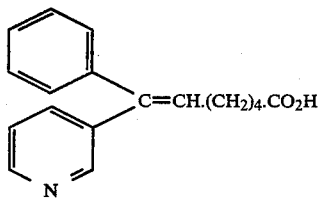 10

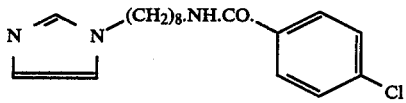 11

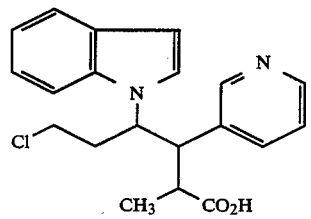 12

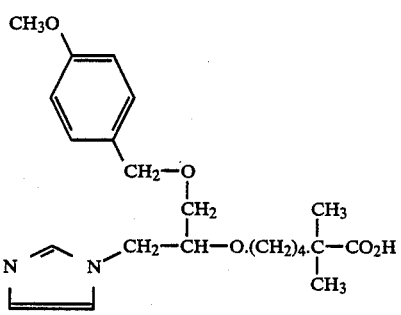 13

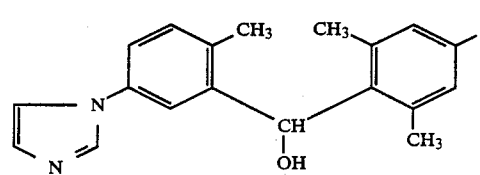 14

What is claimed is:

1. A pharmaceutical composition for use in a disease or medical condition in which thromboxane A2 and/or a related prostanoid constrictor substance is involved which comprises as active ingredients:

(i), an effective amount of 1,3-dioxane ether of the formula

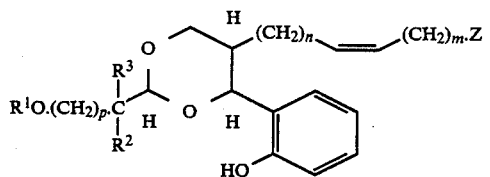 I wherein $R^1$ is (1-6C)alkyl, (3-8C)cycloalkyl, (3-8C)cycloalkyl-1-4C)alkyl, phenyl or phenyl-(1-4C)alkyl, the latter two of which may optionally bear one or two substituents selected from halogeno, (1-4C)alkyl, (1-4C)alkoxy, hydroxy, trifluoromethy, nitro and cyano; $R^2$ and $R^3$ are independently hydrogen or (1-4C)alkyl, or together form (3-6C)polymethylene optionally bearing one or two (1-4C)alkyl substituents; n is 1 or 2; m is 2, 3 or 4; p is zero, 1 or 2; and Z is carboxy or 1(H)-tetrazol-5-yl; and the group at positions 2, 4 and 5 of the dioxane ring have cis-relative stereochemistry; or a pharmaceutically acceptable salt thereof; and (ii), an effective amount of an inhibitor of the synthesis of thromboxane A2 selected from the group consisting of (1) 4-[2-(1H-imidazol-I-yl)ethoxy]benzoic acid (dazoxiben),
(2) sodium 5-(3-pyridylmethyl)benzofuran-2-carboxylic acid (furegrelate),
(3) 3-[3-(1H-imidazol-1-ylmethyl)-2-methyl-1H-indol-1-yl]propanoic acid (UK38485),
(4) 8-[3-methyl-2-(3-pyridyl)-1H-indol-1-yl]octanoic acid (CGS12970),
(5) 5-(5-carboxypentyl)imidazo[1,5-a]pyridine (CGS13080),
(6) 6-[5-chloro-3-methyl-2-(3-pyridyl)-1H-indol-1-yl]hexanoic acid (CGS14854),
(7) (E)-4-(1-imidazolylmethyl)cinnamic acid (OKY046),
(8) sodium (E)-3-[4-(3-pyridylmethyl)phenyl)methacrylate (OKY1580),
(9) (E)-3-[4-(3-pyridylmethyl)phenyl)methacrylic acid hydrochloride (OKY1581),
(10) (E)-7-phenyl-7-(3-pyridyl)-6-heptenoic acid (Cv4151),
(11) N-[(1H)-imidazol-1-yl)octyl]-4-chlorobenzamide,
(12) 1-(3-benzloxy-1(E)-octenyl)imidazole (CBS645),
(13) 2,2-dimethyl-6-[2-(1H-imidazol-1-yl)-1-([4-methoxyphenyl]methoxymethyl)-ethoxy]hexanoic acid (SC41156),
(14) sodium 4-[alpha-hydroxy-5-(1H-imidazol-1-yl)-2-methylbenzyl]-3,5-dimethyl-benzoate (Y20811); having the formulae set out hereinbefore; and the pharmaceutically acceptable salts thereof or, in the case of inhibitor (2), (8), (9) and (14), the salt free form thereof;

together with a pharmaceutically acceptable diluent or carrier.

2. A composition as claimed in claim 1 wherein, in the active ingredient (i), $R^1$ is methyl, ethyl, propyl, butyl, cyclopropyl, cyclobutyl, cyclopentyl, cyclohexyl, cyclopropylmethyl, cyclopentylmethyl, cyclohexylmethyl, phenyl, benzyl or 2 phenylethyl, the latter three of which may optionally bear one or two substituents selected from fluoro, chloro, bromo, methyl, ethyl, methoxy, ethoxy, hydroxy, trifluoromethyl, nitro and cyano: $R^2$ and $R^3$ are independently hydrogen, methyl or ethyl, or together form trimethylene or tetramethylene, optionally bearing one or two methyl substituents: and n, m, p and Z have any of the meanings defined in claim 1.

3. A composition as claimed in claim 1 wherein, in the active ingredient (i), $R^1$ is (1-4C)alkyl, (3-8C)cycloalkyl or phenyl, the latter optionally bearing a substituent selected from halogeno, (1-4C)alkyl, (1-4C)alkoxy, nitro and cyano: $R^2$ and $R^3$ are independently hydrogen or methyl: n is 1; m is 2 or 3; p is zero: and Z is carboxy or 1(H) tetrazol-5 yl.

4. A composition as claimed in claim 1 wherein, in the active ingredient (i), $R^1$ is methyl, ethyl, propyl, cyclopentyl, cyclohexyl or phenyl, the latter optionally bearing a substituent selected from chloro, bromo, methyl, methoxy, nitro and cyano: $R^2$ and $R^3$ are both hydrogen or methyl: n is 1; m is 2; p is zero: and Z is carboxy.

5. A composition as claimed in claim 1 wherein the active ingredient (i) is selected from:
4(Z)-6-([2,45-cis]-4-o-hydroxyphenyl-2-[1-methyl-1phenoxyethyl]-1,3-dioxan-5-yl)hexenoic acid;
4(Z)-6-([2,4,5-cis]4-o-hydroxyphenyl-2-[1-methyl-1propoxyethyl]propoxyethyl]-1,3-dioxan-5-yl)hexenoic acid;
(−)-4(Z)-6-([2,4,5-cis]-4-o-hydroxyphenyl-2-[1-methyl-1phenoxyethyl]-1,3-dioxan-5-yl)hexenoic acid;
and the pharmaceutically acceptable salts thereof.

6. A composition as claimed in claim 1 or 5 wherein the active ingredient (i) is present as a pharmaceutically acceptable salt selected from alkali metal and alkaline earth metal salts, aluminium and ammonium salts, and from salts with organic amines and quaternary bases forming physiologically acceptable cations.

7. A composition as claimed in claim 1 or 5 wherein the active ingredient (ii) is selected from the known inhibitors of thromboxane $A_2$ synthesis, dazoxiben, CV 4151, and the pharmaceutically acceptable salts thereof.

8. A composition as claimed in claim 1 which comprises, as active ingredient (i), 4(Z)-6-([2,4,5-cis]-4-o-hydroxyphenyl-2-[1-methyl-1-phenoxyethyl]-1,3-dioxan-5-yl)hexenoic acid or the laevorotatory optical isomer, or a pharmaceutically acceptable salt thereof; and as, active ingredient (ii), the known inhibitor of thromboxane $A_2$ synthesis, dazoxiben, CV4151, or a pharmaceutically acceptable salt thereof.

9. A method of medical treatment or prophylaxis of a disease or medical condition in which thromboxane $A_2$ and/or a related prostanoid constricto substance is involved in a warm-blooded animal requiring such treatment, which comprises administering to said animal a therapeutically or prophylactically effective amount of an agent (i) comprising a compound of the formula I, or a pharmaceutically acceptable salt thereof, as defined in claim 1 and a therapeutically or prophylactically effective amount of an agent (ii) comprising an inhibitor of thromboxane $A_2$, synthesis, as defined in claim 1.

10. A method as claimed in claim 9 wherein the agent (i) is selected from:
4(Z)-6-([2,4,5-cis]-4-o-hydroxyphenyl-2-[1-methyl-1-phenoxyethyl]-1,3-dioxan-5-yl)hexenoic acid;
4(Z)-6-([2,4,5-cis]-4-o-hydroxphenyl-2-[1-methyl-1-propoxyethyl]-1,3-dioxan-5-yl)hexenoic acid;
(-)-4(Z)-6(* 2,4,5-cis]-4-o-hydroxyphenyl-2-[1-methyl-1-phenyoxyethyl]-1,3-dioxan-5-yl)hexenoic acid;
and the pharmaceutically acceptable salts thereof.

11. A composition as claimed in claim 1 which comprises, as active ingredient (i), 4(Z)-6-([2,4,5-cis]-4-o-hydroxyphenyl-2-[1-methyl-1-phenoxyethyl]-1,3-dioxan-5-yl)hexenoic acid or the laevorotatory optical isomer, or a pharmaceutically acceptable salt thereof; and, as active ingredient (ii), an effective amount of the inhibitor 3-[3-(1H-imidazol-1-ylmethyl)-2methyl-1H-indolyl]propanoic acid (UK38485), or a pharmaceutically acceptable salt thereof.

12. A method as claimed in claim 9 wherein the agent (i) and the agent (ii) are administered to said animal separately.

13. A method as claimed in claim 9 or 12 wherein the agent (i) is selected from the group consisting of
4(Z)-6-([2,4,5 cis]-4-o-hydroxyphenyl-2-[1-methyl-1-enoxyethyl]1,3-dioxan-5-yl)hexenoic acid, the laevorotatory optical isomer thereof, and the pharmaceutically acceptable salts thereof; and the agent (ii) is selected from the group consisting of 4 [2-(1H-imidazol-1-yl)ethoxy]benzoic acid (dazoxiben), (E)-7-phenyl-7-(3-pyridyl)-6-heptenoic acid (Cv4151), and the pharmaceutically acceptable salts thereof.

14. A method as claimed in claim 9 or 12 wherein the agent (i) is selected from the group consisting of
4(z) 6 ([2,4,5-cis]4-o-hydroxyphenyl-2-[1-methyl-I-phenoxyethyl]-1,3-dioxan-5-yl)hexenoic acid, the laevorotatory optical isomer thereof, and the pharmaceutically acceptable salts thereof; and the agent (ii) is selected from the group consisting of 3-[3-(1H-imidazol-1-ylmethyl)-2-methyl-1H-indol-1-yl]propanoic acid (UK38485), and the pharmaceutically acceptable salts thereof.

* * * * *